(12) United States Patent
Owen (10) Patent No.: US 9,463,891 B2
(45) Date of Patent: Oct. 11, 2016

(54) METHOD AND APPARATUS FOR SEPARATING INDIVIDUAL SEALED TUBES FROM AN ARRAY OF TUBES SEALED WITH A MEMBRANE

(71) Applicant: TAP Biosystems (PHC) Limited, Hertfordshire (GB)

(72) Inventor: Justin Michael Owen, Cambridge (GB)

(73) Assignee: TAP BIOSYSTEMS (PHC) LIMITED, Royston, Hertfordshire (GB)

( * ) Notice: Subject to any disclaimer, the term of this patent is extended or adjusted under 35 U.S.C. 154(b) by 741 days.

(21) Appl. No.: 13/798,958

(22) Filed: Mar. 13, 2013

(65) Prior Publication Data
US 2013/0247514 A1    Sep. 26, 2013

(30) Foreign Application Priority Data

Mar. 16, 2012 (GB) .................................. 1204682.7

(51) Int. Cl.
| | |
|---|---|
| B65B 61/06 | (2006.01) |
| B65B 51/10 | (2006.01) |
| B01L 3/00 | (2006.01) |
| G01N 35/00 | (2006.01) |
| G01N 35/04 | (2006.01) |

(52) U.S. Cl.
CPC .......... B65B 61/065 (2013.01); B01L 3/50853 (2013.01); B01L 3/50855 (2013.01); B65B 51/10 (2013.01); G01N 35/0099 (2013.01); B01L 2300/044 (2013.01); B01L 2300/0672 (2013.01); G01N 2035/041 (2013.01); Y10T 83/2133 (2015.04)

(58) Field of Classification Search
CPC .......... Y10T 83/2133; B01L 3/50853; B01L 2300/0672; B01L 2300/044; B01L 3/50855; B01L 2300/0829; B65B 61/065; B65B 61/06; B26F 1/40; A21C 11/10; B21D 28/28; B21D 28/30; B21D 7/1818
USPC .......... 53/329.3; 422/569, 400, 99; 436/174; 83/123–128, 653, 684
See application file for complete search history.

(56) References Cited

U.S. PATENT DOCUMENTS

| | | |
|---|---|---|
| 4,282,698 A | 8/1981 | Zimmermann |
| 5,682,729 A | 11/1997 | Buchko |

(Continued)

FOREIGN PATENT DOCUMENTS

| | | |
|---|---|---|
| CN | 202290116 U | 7/2012 |
| EP | 0904841 A2 | 3/1999 |

(Continued)

*Primary Examiner* — Xavier A Madison
(74) *Attorney, Agent, or Firm* — Dickinson Wright PLLC (57) ABSTRACT

Apparatus (10) for separating individual sealed tubes (42) from an array has rack support (30) for supporting an array of tubes with their upper rims (43) disposed in a horizontal plane and all sealed with a sealing membrane (90), and a punch station (60) comprising a punch tool (62) with cutting edge (66). Cutting edge (66) pierces through membrane (90) from above to separate an individual sealed tube (42) from the remainder of the membrane. The tool has multiple cutting edges (66) in a linear array corresponding to a column of a tightly-packed x by y array of tubes in the rack (40) to simultaneously separate the tubes (42) of a whole column. The cutting edge (66) starts piercing membrane (90) at the corners (43*a*) of each tube rim and progressively shears through the membrane. Ejector pins (68) retain the separated tubes within the rack (40).

20 Claims, 8 Drawing Sheets

(56) References Cited

U.S. PATENT DOCUMENTS

| | | |
|---|---|---|
| 6,435,582 B1 | 8/2002 | DaSilva et al. |
| 2002/0021986 A1* | 2/2002 | McCall ............... B01L 3/50853 422/400 |
| 2002/0102736 A1 | 8/2002 | Kittock et al. |
| 2005/0026295 A1* | 2/2005 | Harding .................... B01L 9/06 436/43 |
| 2005/0063874 A1* | 3/2005 | Smith ................. B01L 3/50853 422/400 |
| 2007/0172393 A1 | 7/2007 | Beer |
| 2010/0028214 A1 | 2/2010 | Howard et al. |

FOREIGN PATENT DOCUMENTS

| | | |
|---|---|---|
| EP | 1348485 A1 | 10/2003 |
| EP | 1516669 A1 | 3/2005 |
| JP | 2005-224906 A | 8/2005 |
| JP | 2006-026851 A | 2/2006 |
| WO | 0202405 A1 | 1/2002 |

* cited by examiner

METHOD AND APPARATUS FOR SEPARATING INDIVIDUAL SEALED TUBES FROM AN ARRAY OF TUBES SEALED WITH A MEMBRANE

FIELD OF THE INVENTION

The present invention relates generally to the separation of individual tubes from an array of tubes that have been sealed with a membrane, especially large arrays of small tubes.

BACKGROUND TO THE INVENTION

In biological and chemical assay processes and systems which operate with tubes containing samples of biological or chemical material it is important that the contents of the tubes remain isolated from the atmosphere in the lab and during storage so that the contents do not evaporate or become contaminated with foreign bodies. Therefore, it is common practice to seal tubes. This may be performed with a sealing membrane that, once punctured must be replaced, or it may be with a resealable membrane.

When the samples contained within the tubes are not subjected to frequent access, then a sealing membrane that is not resealable is sufficient. The sealing membrane may take the form of a foil, backed with an adhesive that may be heat or pressure sensitive. In order to apply such a sealing membrane to a tube, it is usual to bring the top of the tube into contact with a sealing membrane that has been treated with such an adhesive and then to apply heat or pressure, as applicable, to cause the adhesive to adhere to the top of the tube. In general it is often necessary to seal a large number of tubes at the same time and therefore the sealing membrane is applied to an array of tubes that are localised in a supporting storage rack. However, the racks in which the tubes are placed are designed to make the most economical use of space possible and therefore the upper rims at the tops of the tubes are often in close contact. Very accurate registration and positioning of the tubes is essential.

As technology advances it is possible to process smaller samples and therefore there is a growing demand for smaller tubes, exacerbating these problems. This has led to the situation where it is difficult to seal and separate a large number of very small tubes held in a rack.

In order to separate the sealed tubes in such close contact it has been found to be necessary to use an array of spring-loaded pins arranged beneath the storage rack for pressing a number of the tubes out of the rack into contact with a sealing membrane disposed above the plate, a hot platen relatively movable into contact with the sealing membrane to melt the sealing membrane to the tops of the tubes that have been raised from the rack by the pins, and a die plate with holes movable relatively past the tops of the newly sealed tubes in order to cut the sealing membrane around each tube and thus separate the sealed tubes from the remainder of the sealing membrane.

In order for there to be enough scrap sealing membrane left for it to remain intact with sufficient strength to be easily removed from the device without disintegration after the sealing and separation steps, the pins may be actuated to raise the tubes from the rack in a checkerboard pattern. This facilitates the use of the sealing membrane in the form of a continuous web that can be fed from a reel into the apparatus with the resultant scrap sealing membrane being wound onto a second reel.

Such automation of the sealing and separation of large arrays of small tubes requires relatively complex equipment, and in particular requires complex, moving, precision parts to be located both above and below a rack holding the array of tubes.

The use of a checkerboard pattern also results in a significant proportion of the continuous web of sealing membrane being wasted.

Accordingly, it is an object of the invention to provide a simplified apparatus and associated method for separating individual sealed tubes from an array. Another object of the invention is the reduction of waste sealing membrane.

SUMMARY OF THE INVENTION

According to a first aspect of the invention, there is provided a punch tool for separating individual tubes from an array of tubes within a storage rack, wherein upper rims of the tubes are sealed with a sealing membrane extending across the array, the punch tool having:
  a tool body;
  a cutting edge on a lower side of the tool body, configured to pierce through the sealing membrane around one of the sealed tube rims so as to separate the associated sealed tube from the remainder of the sealing membrane; and
  an ejector pin insertable inside the cutting edge so as to be urged against the tube rim of the separated sealed tube.

The thin cutting edge fits closely around the associated tube rim, which enables the cutting edge to be lowered relative to the array from above and to insert between adjacent tube rims. This enables one or more tubes to be separated from the other tubes in a sealed array, where those tubes were all connected by a single sealing membrane, without requiring anything other than a support beneath the array. The tool can be used on arrays in which the tube rims are closely packed. This results in as little as zero waste of the sealing membrane, because each portion of the sealing membrane is used to seal a corresponding tube lid.

The tool may be used manually, which is to say aligned by sight to an array of tubes within a storage rack and pushed downwardly so as to separate the desired sealed tube from the remainder of the sealing membrane and hence from the other tubes in the array. Alternatively, the tool may be operated for example by a robot arm, programmed to align the tool to a series of the tubes in the array to separate them from the sealing membrane in turn.

The ejector pin is provided to eject the separated sealed tube from inside the cutting edge, where it is most likely held by friction. The ejector pin is preferably resiliently mounted to the tool body inside the cutting edge so as to be urged against the tube rim of the separated sealed tube with a predefined force. In this arrangement, the piercing of the membrane to separate the sealed tube and the ejection of the sealed tube from the cutting edge can be achieved in a single action.

Typically, the tool has a plurality of cutting edges configured to pierce through the sealing membrane around a corresponding plurality of the sealed tube rims so as to separate the respective sealed tubes individually and simultaneously from the remainder of the sealing membrane. The plurality of cutting edges may comprise a linear array for separating a corresponding linear array of tubes, or may comprise a 2D array for separating a corresponding 2D array of tubes. By having a plurality of cutting edges, the tool is able to separate a corresponding plurality of tubes from the sealing membrane in a single action.

The or each cutting edge is preferably profiled so as to cut through the sealing material in a progressive shearing action. This keeps the punching force required to pierce and cut the sealing membrane to a minimum, which is especially important where a large number of tubes are being separated from the membrane simultaneously. This also helps to maintain a clean cut and hence to ensure proper sealing of the tubes.

Preferably, the or each cutting edge is substantially rectangular, comprising a piercing tip at each corner, and an inverted U- or V-shaped blade extending between adjacent piercing tips. This configuration is ideal for separating correspondingly rectangular tubes that are tightly packed into a storage rack. Such rectangular tubes typically have a radius at each upper corner. Thus, adjacent upper corners of the tubes in the array define a regular pattern of spaces in the array. The piercing tip at each corner of the cutting edge is received in the spaces in the array surrounding the targeted tube or tubes. This does two things: it helps to ensure a proper alignment of the punch tool to the tube or tubes to be separated—a significant amount of initial misalignment can be accommodated; and it ensures that the initial piercing force is low. The inverted U- or V-shaped cutting edge profile means that as the punch tool is lowered further, the cutting edge(s) shear through the sealing membrane progressively to make a clean, low-force cut, whilst also aligning the tool accurately to the rim(s) of the tube(s) being separated.

The punch tool may further comprise a compression plate surrounding the cutting edge and having a flat lower surface resiliently mounted to the tool body so as to be urged against the web of sealing membrane with a predefined force. This compression plate, or 'shoe', ensures that the sealing membrane near the cutting edge is held with a sufficient tension to prevent distortion. This helps to ensure a clean cut.

According to a second aspect of the invention, there is provided an apparatus for separating individual sealed tubes from an array of tubes sealed with a membrane, the apparatus comprising:

a rack support for supporting an array of tubes within a storage rack within the apparatus, wherein upper rims of the tubes are disposed in a plane; and a punch station comprising a punch tool in accordance with the first aspect of the invention;

wherein the cutting edge is moveable relative to the rack support to a position overlying the rack support and perpendicular to the plane between a position above the plane and a position below the plane.

This facilitates automation of the tube separation process.

Typically, the rack support supports the array of tubes within a storage rack horizontally within the apparatus, the upper rims of the tubes being in a horizontal plane. The tubes cannot be supported at too great an angle from horizontal because their contents would then be liable to spilling over the upper rims. In this embodiment, the cutting edge is moveable relative to the rack support horizontally to a position overlying the rack support and vertically between the positions above and below the plane.

Whereas the apparatus may be used to separate tubes form a pre-sealed array within a storage rack, i.e. a rack containing an array of tubes all sealed by a single sealing membrane, it could be preferable to have a single apparatus capable of both sealing the tubes and then separating them. Thus, the apparatus may further comprise a sealing station having a platen with a lower platen surface moveable relative to the rack support to a position overlying the rack support and between a position above the plane and a position substantially aligned with the plane, wherein the platen when in the position overlying the rack support and substantially aligned with the plane is configured to apply heat and/or pressure to the sealing membrane for sealing the membrane to the rims of a plurality of the tubes. Where the upper rims of the tubes are supported in a horizontal plane, the lower platen surface is moveable relative to the rack support horizontally to a position overlying the rack support and vertically between the positions above and substantially aligned with the plane.

Although it is envisaged that the sealing membrane could be supplied to the array of tubes manually, for example by placing a single sheet of sealing membrane over the top of the array, it would be preferable to automate the process. To this end, the apparatus may further comprise a sealing membrane transport mechanism for supplying a web of sealing membrane to the sealing station, whereby at least a portion of the web of sealing membrane is disposed between the lower platen surface and the plane.

Whereas it is envisaged that the punch station and/or, where included, the sealing station may be moved relative to a fixed storage rack, typically the punch station and the sealing station will each be at respective fixed locations, with the apparatus further comprising a rack support transport assembly for transporting a storage rack within the rack support in the apparatus, to the sealing station and then to the punch station. Where the rack is supported horizontally, the punch station and the sealing station will each be at respective fixed horizontal locations, and the rack support transport assembly would transport the storage rack horizontally. If the rack is supported at an angle off horizontal, then the relative movements would be adapted accordingly.

The lower platen surface of the sealing station may be sized so as to seal the sealing membrane to a whole array of tubes simultaneously. Alternative arrangements, such as sealing half of the array at a time with a smaller platen can be envisaged, but would result in longer operating cycles.

The array of tubes typically comprises a regular array of x columns by y rows of tubes. This is standard in the industry. For example, a 24×16 array contains 384 tubes. Alternative arrangements include staggered arrays, in which one column of, for example, circular-rimmed tubes is offset against its neighbouring columns to maximise the packing density of the tubes in the array.

The tubes typically have substantially rectangular upper rims. This enables the tubes to be tightly packed in the array in contrast, for example, to circular-rimmed tubes. Other tessellating shapes, such as triangles or hexagons, could also be used.

Where there is a linear array of cutting edges, it may be configured to pierce around each of the sealed tube rims of a column of the array simultaneously. This arrangement only requires relative motion between the punch tool and the rack support along an axis perpendicular to the columns in the array to separate all tubes from the array. To facilitate this relative motion, where there is a rack support transport assembly, it may be further configured to index the rack support at the punch station by the pitch of a column so as to align the cutting edge with the next column in the array.

Whereas the apparatus could work by supplying a series of sheets of sealing membrane to consecutive arrays of tubes, it would be operationally more efficient for the web of sealing membrane to be supplied from a continuous roll and for the sealing membrane transport mechanism to be configured to move the continuous web together with the storage rack during the transport of the storage rack from the sealing station to the punching station and, where the rack transport assembly is further configured to index the storage rack at the punch station, during that indexing. This arrangement ensures a synchronised movement of the array of tubes with the sealing web, such that that the tension in the sealing web will not get too high.

To further assist in aligning the punch tool to the tubes in the array, the punch tool may include a datum spike for receipt in a mating hole in the rack support for alignment of the punch tool with the rack support.

The punch tool may be mounted to the apparatus with lateral float so as to accommodate some initial misalignment of the punch tool, specifically the cutting edge(s) thereof, with the tubes in the array.

According to a third aspect of the invention, there is provided a method of separating individual sealed tubes from an array of tubes sealed with a membrane, the method comprising the steps of:

supporting the array of tubes within a storage rack, upper rims of the tubes being disposed in a plane;
translating the storage rack relative to a punching station having a punch tool with a cutting edge on a lower side of a tool body; and,
at the punching station:
moving the cutting edge perpendicularly to the plane relative to the storage rack from a position above the plane to a position below the plane, thereby piercing around one of the sealed tube rims so as to separate the associated sealed tube from the remainder of the sealing membrane;
during the piercing movement, urging an ejector pin of the punch tool to move towards the tool body against a biasing force through contact of the ejector pin on the rim of the separated sealed tube; and
moving the cutting edge perpendicularly to the plane relative to the storage rack from the position below the plane to a position above the plane, the biasing force urging the ejector pin away from the tool body to urge the separated sealed tube to remain in the storage rack.

The method may further include a step of sealing the array of tubes with the membrane prior to the piercing step, comprising:

supplying a web of sealing membrane to a sealing station; and,
at the sealing station, sealing at least a portion of the web of sealing membrane to a plurality of the rims of the tubes in the array simultaneously by the application of heat and/or pressure.

The web of sealing membrane may be continuous.

The method may further include a step of translating the storage rack relative to the sealing station.

The method may further include a step of translating the storage rack from the sealing station to the punching station.

The method may be carried out using the apparatus of the second aspect of the invention.

According to a fourth aspect of the invention, there is provided a gripper tool for selectively lifting individual tubes from an array of tubes within a storage rack, comprising:

a gripper tool body;
a separating edge on a lower side of the tool body, configured to insert between adjacent tubes in the array and to grip an outer surface of a selected tube with an interference fit; and
an ejector pin mounted to the gripper tool body inside the separating edge and actuatable from a raised position, in which the selected tube can be received within the separating edge, and a lowered position, in which the selected tube is prevented from being received in the separating edge or, if already received therein, is ejected therefrom.

The gripper tool may additionally be for separating individual tubes from an array of tubes within a storage rack, wherein upper rims of the tubes are sealed with a sealing membrane extending across the array, wherein the separating edge comprises a cutting edge, configured to pierce through the sealing membrane around the selected sealed tube rim so as to separate the associated sealed tube from the remainder of the sealing membrane prior to gripping the outer surface of the tube with an interference fit. In this regard, the gripper tool essentially corresponds to the punch tool of the first aspect of the invention, only the optional resiliently-biased ejector pins of the first aspect are replaced by the selectively actuatable ejector pins.

The gripper tool may further comprise a plurality of separating edges configured to grip a corresponding plurality of selected tubes so as to grip the respective selected tubes individually and simultaneously. The plurality of separating edges may either comprise a linear array for gripping a corresponding linear array of selected tubes, or 2D array for gripping a corresponding 2D array of tubes.

According to a fifth aspect of the invention, there is provided a method of lifting individual selected tubes from an array of tubes within a storage rack, the method comprising the steps of:

supporting the array of tubes within the storage rack, upper rims of the tubes being disposed in a plane;
translating the storage rack relative to a gripping station having a gripping tool with a separating edge on a lower side of a gripping tool body configured to insert between adjacent tubes in the array;
at the gripping station:
raising an ejector pin within the separating edge;
moving the separating edge perpendicularly to the plane relative to the storage rack from a position above the plane to a position below the plane, thereby gripping an outer surface of a selected tube with an interference fit;
during the piercing movement, urging an ejector pin of the punch tool to move towards the tool body against a biasing force through contact of the ejector pin on the rim of the separated sealed tube; and
moving the separating edge perpendicularly to the plane relative to the storage rack from the position below the plane to a position above the plane, friction between the separating edge and the selected tube causing the selected tube to be moved with the gripper tool; moving the gripping tool to a dispense location; and,
at the dispense location, actuating the ejector pin to a lowered position, thereby ejecting the selected tube from the gripping tool.

The method may be carried out using the gripper tool of the fourth aspect of the invention. In particular, the method may be carried out using the modified punch tool such that the method includes the step of piercing the sealing membrane just prior to gripping the selected tube(s).

BRIEF DESCRIPTION OF THE DRAWINGS

The invention will be described, by way of example, with reference to the accompanying drawings, in which:

FIG. 5b is a detail view of a portion of FIG. 4a;

FIG. 8a is a schematic cross-section through the punch station, showing the sealed array of tubes supported at a position in which a first column of the array is disposed beneath a punch tool in a raised position;

FIG. 8b is a detail view of a portion of FIG. 8a;

FIG. 9a corresponds to FIG. 8a, but showing the punch tool in a lowered position, piercing the membrane around each of the tubes in the column;

FIG. 9b is a detail view of a portion of FIG. 9a;

DETAILED DESCRIPTION

Figure 1:
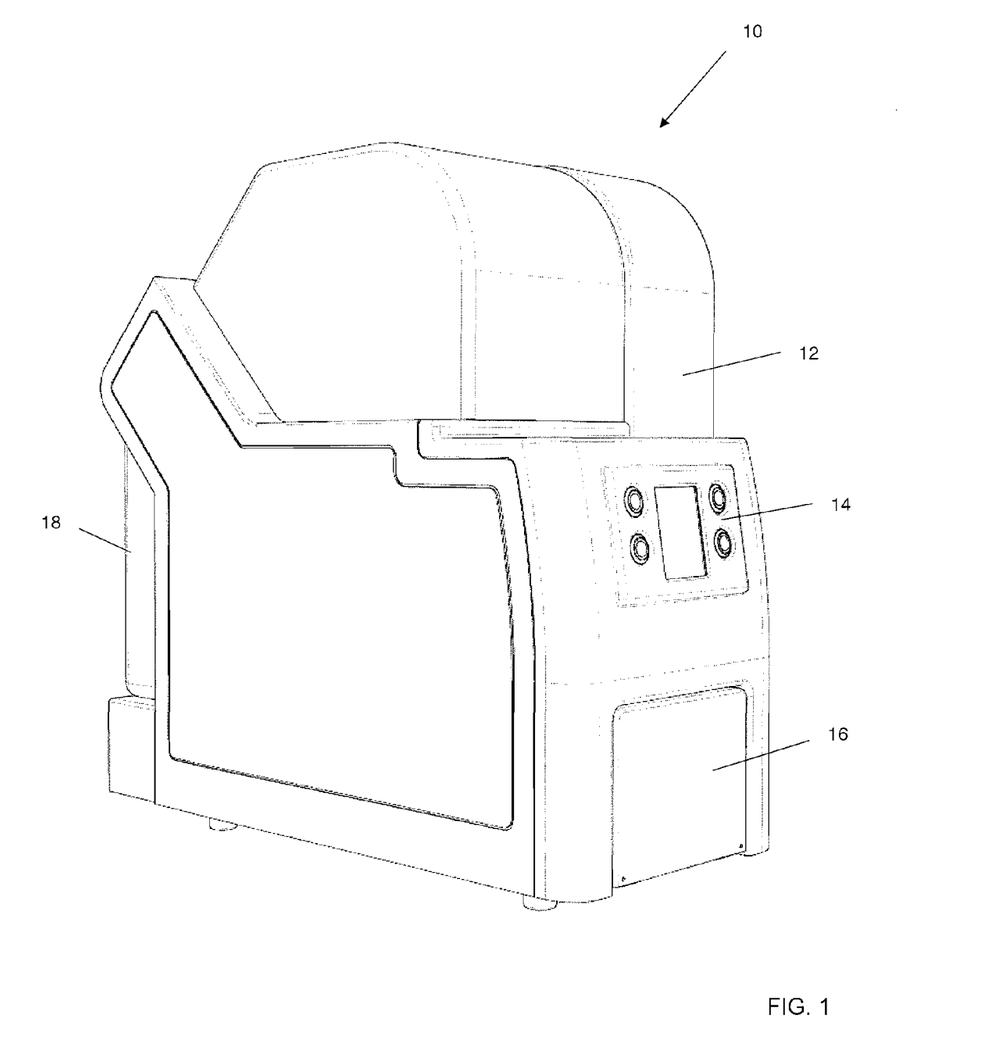
FIG. 1 is a perspective view of an apparatus for sealing and separating tubes from an array.

As shown in FIG. 1, an apparatus 10 for automated sealing and separation of an array of tubes comprises, generally, an outer cover 12 surrounding an interior. A control panel 14 is positioned on a front side of the apparatus for a user to control operation of the apparatus. A hinged hatch 16 on the front side provides access to the interior of the apparatus. A removable bin 18 is provided at the opposite, rear side of the apparatus.

Figure 2:
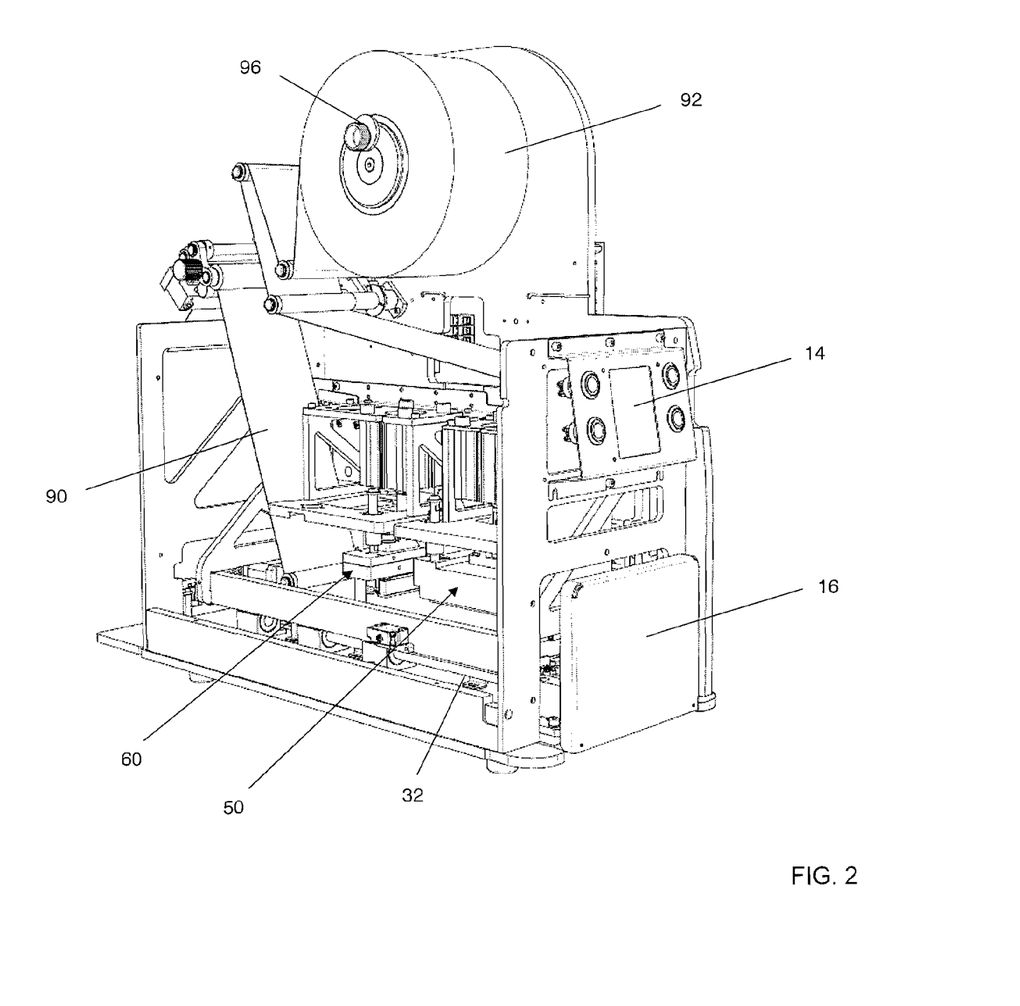
FIG. 2 corresponds to FIG. 1, but with the outer cover removed to show interior mechanisms.
Figure 3:
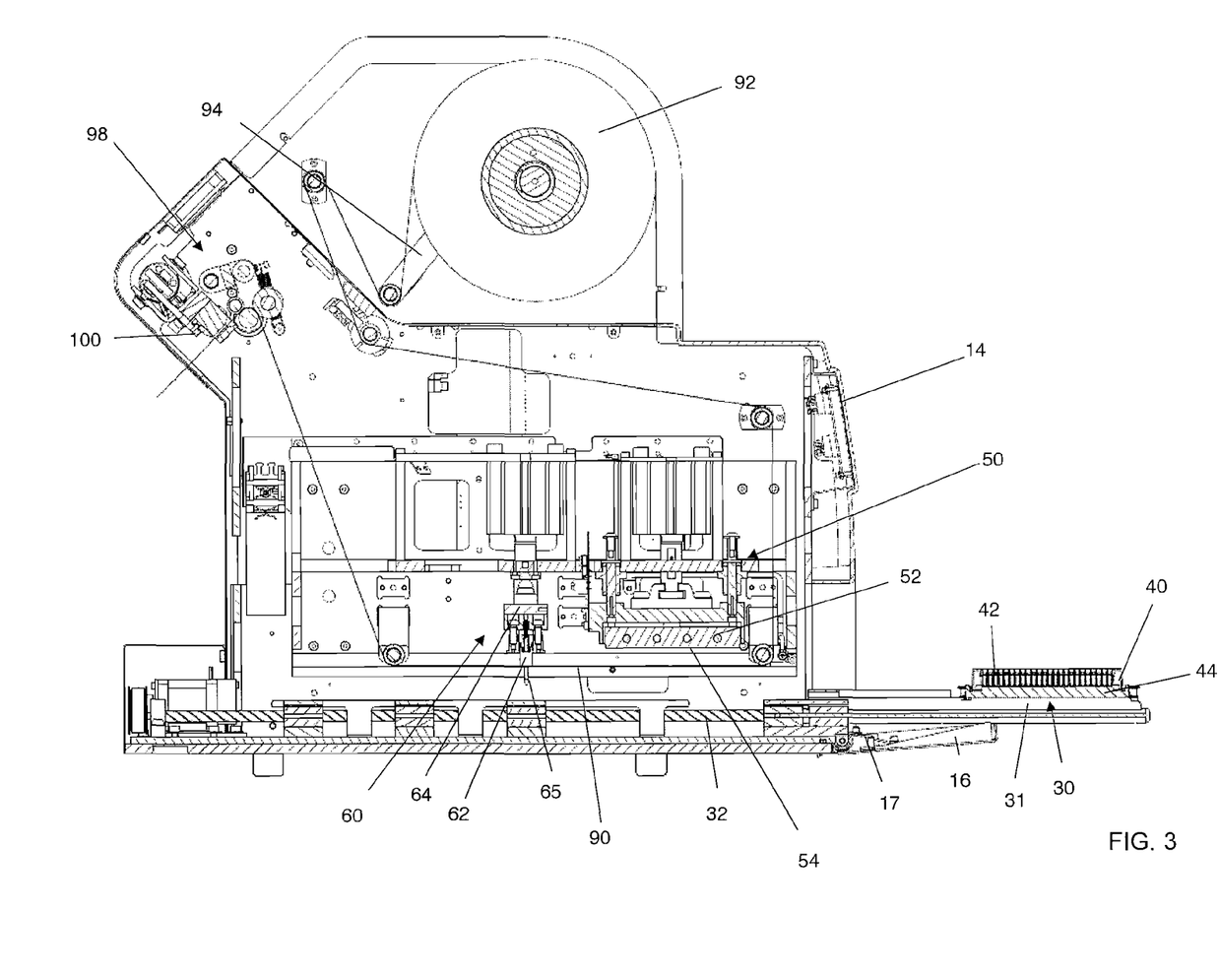
FIG. 3 is a cross-section through the apparatus.

FIGS. 2 and 3 show the interior of the apparatus 10. In FIG. 3, the hatch 16 is hinged open, with a rack support 30 projecting out of the interior for loading and unloading of a storage rack 40 containing an array of tubes 42 in an x by y array. The storage rack 40 is mounted to the rack support 30 via a rack nest 44, with respective datum features provided to ensure proper alignment of the rack 40 with the support 30. The rack 40 may also be retained in the rack nest 44 with a clamp (not shown).

The rack support 30 comprises a carriage 31 that is moveable into and out of the apparatus 10 by means of a stepper motor-driven lead screw 32 parallel to the rows of the tubes 42 in the rack 40, perpendicular to the columns thereof. The rack support carriage 31, and therefore the array of tubes 42 within a storage rack 40 is thus translated horizontally in the apparatus with upper rims 43 of the tubes 42 in the array being disposed in a horizontal plane. Movement of the rack support carriage 31 out of the apparatus automatically opens the hinged hatch 16, against the closing action of a spring 17. When the rack support carriage 31 is moved back into the interior of the apparatus, the spring 17 urges the hatch 16 to close behind it.

A sealing station 50 comprises a platen 52 vertically moveable from a raised position to a lowered position, the platen 52 having a lower platen surface 54 that covers the x by y array of tubes in the rack 40.

A punch station 60 comprises a punch tool 62 having a tool body 64, a cutting edge 66 on a lower side of the tool body, and an ejector pin 68 resiliently mounted via a spring 69 to the tool body 64 inside the cutting edge 66. Each ejector pin 68 has a dished lower surface, defining a lower edge 68a.

Figure 4:
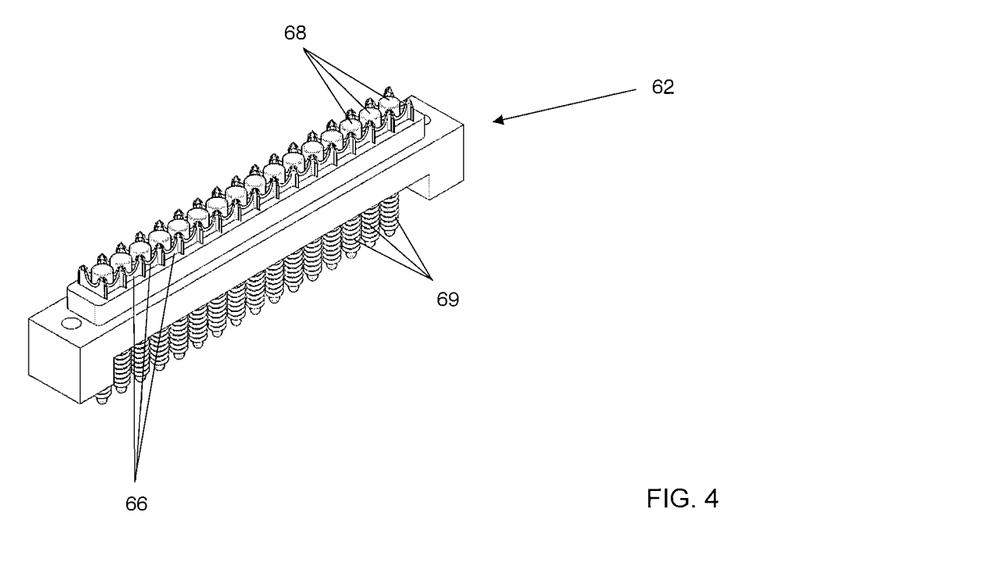
FIG. 4 is a perspective view of a punch tool used in the apparatus of FIGS. 1-3.
Figure 5A:
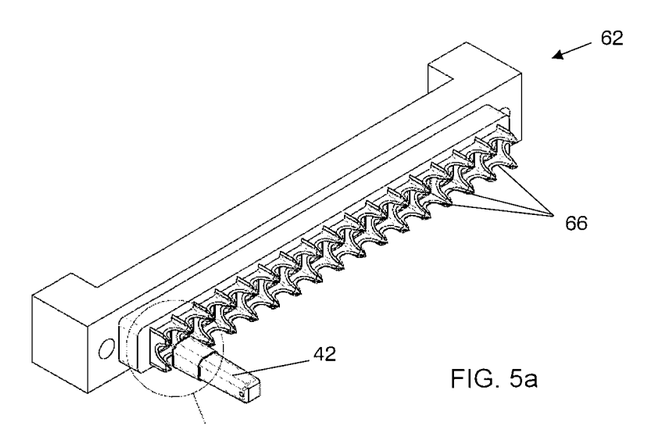
FIG. 5a is another perspective view of the punch tool, showing a cutting edge at the lower end of the tool together with a single tube, sprung ejector pins being omitted for clarity.
Figure 5B:
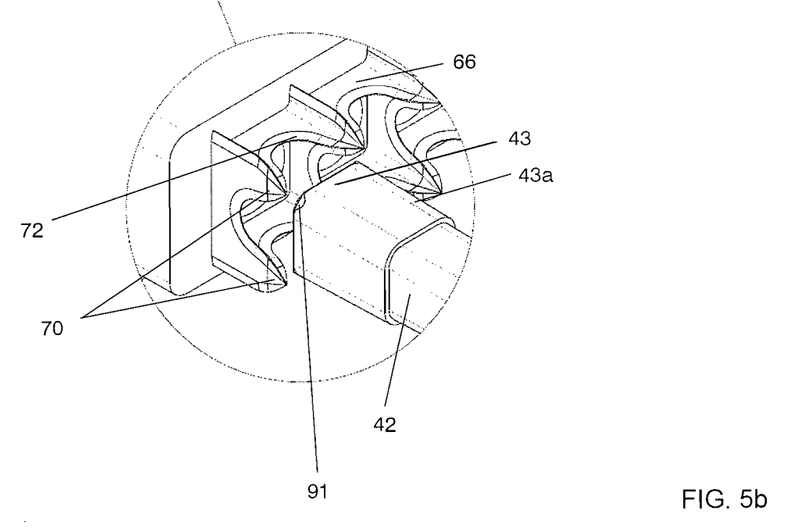

As best seen in FIGS. 4 and 5, the punch tool 62 has a plurality of cutting edges 66 in a linear array. The illustrated punch tool 62 has 16 cutting edges 66 and 16 associated ejector pins 68, corresponding to the 16 tubes 42 in a single column of a 24×16 array of tubes. Of course, other numbers of cutting edges 66 may be used instead, either to correspond to a single column of a differently configured array of tubes, or to correspond to just a portion of a column. Rather than being arranged in a linear array, the plurality of cutting edges could be arranged in a 2D array, corresponding to a multiple number of whole columns of tubes, or to a multiple number of partial columns. A single cutting edge 66, corresponding to a single tube 42 could be used, but would require multiple punch operations to result in the same number of separated tubes 42.

For an array of tubes 42 having rectangular rims 43, the or each cutting edge 66 comprises a corresponding rectangle. Of course, other rim profiles are envisaged, with corresponding cutting edge profiles. As illustrated, the rims 43 are substantially square, but with a radius 43a at each corner. The cutting edge thus comprises a piercing tip 70 at each corner, with a curved inverted U-shaped blade portion 72 extending between adjacent tips 70. Adjacent cutting edges 66 share a blade 72, which would pierce between adjacent tubes 42. Rather than having a curved inverted U-shape, each blade portion 72 may instead have a more linear V-shape. The important factor is for the cutting edge 66 to cut through the sealing material with a progressive shearing action, beginning at the piercing tips 70, and progressing along the blades 72. With a U- or V-shaped blade 72, the cuts would finish centrally at each side of the rim 43. Other blade profiles could be envisaged.

The punch tool 60 includes a compression plate or 'shoe' 80 surrounding the cutting edges 66 and having a flat lower surface 82. The compression plate 80 is mounted to the punch tool body 62 via springs 84 so as to be urged away from the tool body 62 with a predefined force.

A sealing membrane transport mechanism supplies a web of sealing membrane 90 to the sealing station 50 such that at least a portion of the web 90 is disposed horizontally between the lower platen surface 54 and the rim tubes 43. The web is typically supplied in continuous form from a roll 92, with suitable tension-adjustment mechanisms such as a dancing arm 94 and a friction disc 96, the web 90 being pulled through the apparatus by a drive mechanism 98, such as a pinch roller. A guillotine 100 downstream of the web drive mechanism 98 is actuated to chop the waste web material into pieces for receipt in the removable bin 18.

In operation, an operator specifies the type of rack to be sealed and/or punched, for example specifying the number of tubes 42 in the array, their configuration as an array, and their size. One or more of these specifications may be detected automatically by the provision of appropriate sensors.

At a first step, the rack support carriage 31 is moved out of the apparatus to a loading position. The operator loads a storage rack 40 full of tubes 42 into a rack nest 44 on the support carriage 31. The loaded carriage is then translated horizontally, by operation of the lead screw 32, into the interior of the apparatus and to a position at the sealing station 50 such that the lower surface 54 of the platen is overlying the rack support 30 in registration with the array of tubes 42.

Figure 6:
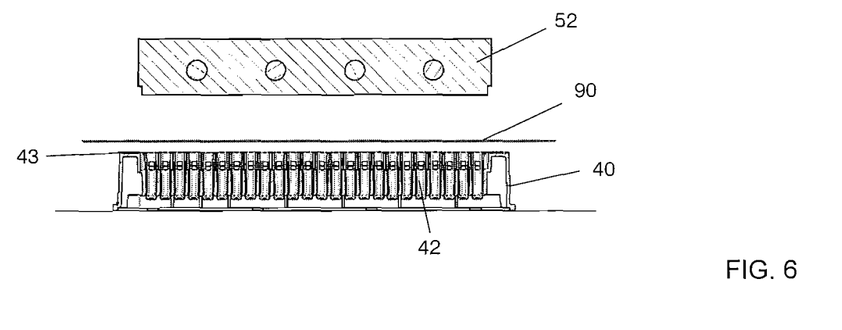
FIG. 6 is a schematic cross-section through the sealing station, showing an array of tubes in a supported storage rack, a platen in a raised position, and a web of sealing membrane disposed between the raised platen and the array of tubes.
Figure 7:
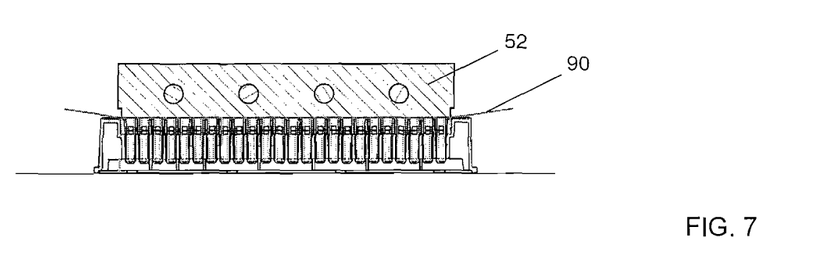
FIG. 7 corresponds to FIG. 6, but showing the platen in a lowered position, sealing the membrane to the tops of the tubes in the array.

With reference in particular to FIGS. 6 and 7, the platen 52 is lowered from the raised position to a position in which the lower platen surface 54 is brought into engagement with the rims 43 of the tubes, the application of heat and/or pressure (depending on the type of sealing membrane being used) sealing the portion of web 90 interposed between the platen 52 and the array of tubes 42 to the rims 43 of the tubes. The pressure, heat and duration of contact can all be controlled to ensure a proper seal.

Once sealed, the platen 52 is raised again to allow the rack support 30 to move out of the sealing station 50.

Figures 8A, 8B:
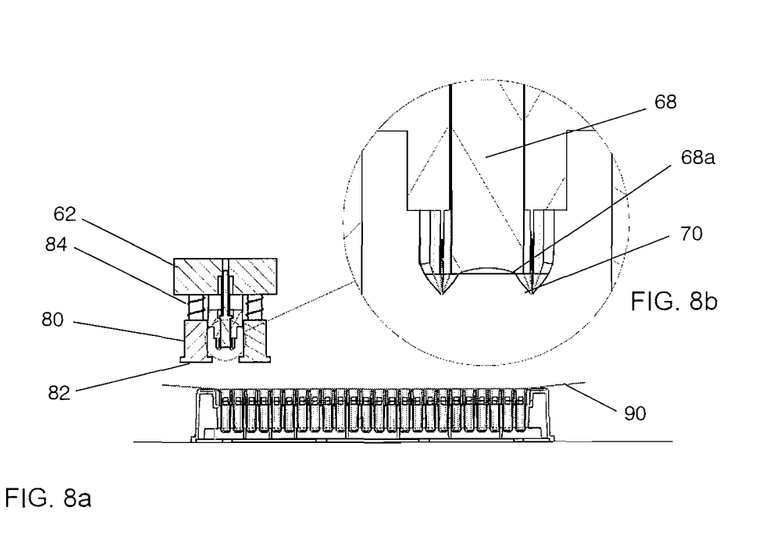
Figures 9A, 9B:
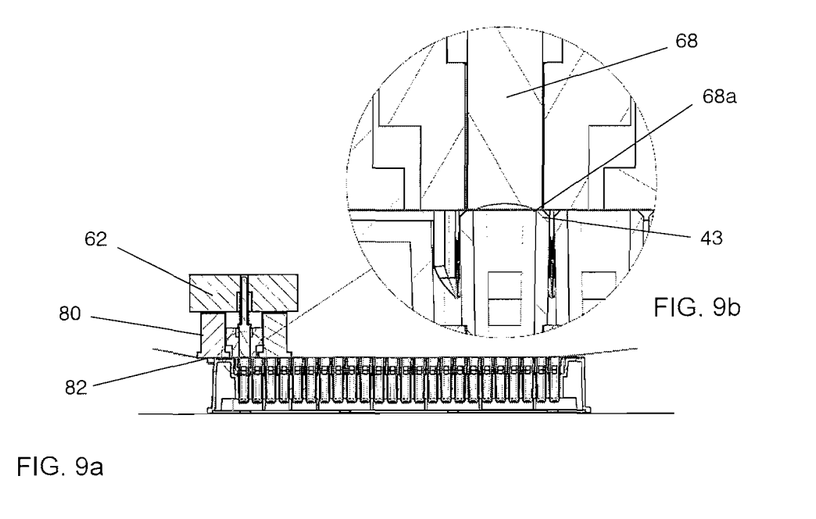

Next, with reference in particular to FIGS. 8 and 9, the rack support 30 with the sealing web 90 attached to the array of tubes is translated horizontally, by operation of the lead screw 32, further into the interior of the apparatus to a position at the punch station 60 such that first column of the array of tubes 42 is in registration with the cutting edges 66 of the punch tool 62. The punch tool 62 is lowered from the raised position towards the rack support 30.

During the lowering movement, datum spikes 65 projecting downwardly from opposite ends of the punch tool 62 are received in mating holes (not shown) in the rack support 30 for alignment of the punch tool with the rack support. The mating holes may be through the rack nest 44 and/or through the support carriage 31.

The compression plate 80 comes into contact with the sealing web 90 over the tube rims 43. Continued downward motion of the punch tool 62 compresses the compression plate springs 84 against the tool body 64. The flat lower surface 82 of the compression plate 80 is therefore urged against the web of sealing membrane 90 with the predefined force of the springs 84. This tensions the membrane near the cutting edges 66 so that it is held with a sufficient tension to prevent distortion.

Further continued downward motion of the punch tool 62 brings the cutting edges 66 into contact with the tensioned portion of web membrane 90, first piercing at the four corners of each tube rim 43. As the punch tool 62 is lowered further, each cutting edge 66 pierces through the sealing membrane around the associated sealed tube rim 43 so as to separate the associated sealed tube 42 from the remainder of the sealing membrane 90. In the illustrated embodiment, a whole single column of the array is punched simultaneously. As seen in FIG. 5b, a lip 91 of the sealing membrane is flattened against the radiused corner 43a of the tube rim 43.

During the separation of the tubes 42 in the column from the remainder of the array, the downward motion of the punch tool 62 brings the ejector pins 68 into contact with the tops of the respective sealed tubes 42. More particularly, the lower edges 68a of the ejector pins bear against the tops of the tube rims 43, albeit with the sealing membrane disposed in between. As the downward motion continues, to cut the sealing membrane in the progressive shearing action, the ejector pin springs 69 are compressed against the tool body 64. The lower edges 68a of the ejector pins 68 are therefore urged against the now separated tube rims 43 with the predefined force of the ejector springs 69.

Once the column of tubes has been punched (separated), the punch tool 62 is raised back to its initial raised position. During this raising motion, friction between the separated tubes 42 and the surrounding cutting edges 66 tends to cause the separated tubes 42 to rise with the punch tool. However, the spring force of the ejector pin springs 69 is selected so that the ejector pins 68 push against the separated tubes with enough force to overcome the friction, thereby retaining the separated tubes 42 within the rack 40.

The rack support 30 is then indexed the pitch of a column to a position in which the next column in the array of tubes lies beneath the punch tool 62 and the process is repeated until all columns have been punched and each tube 42 has been separated from each other and results in an array of individual sealed tubes, at which point the rack support 30 is ejected from the interior of the apparatus through the hatch for unloading of the finished rack 40 by the operator.

During movement of the rack support 30 from the sealing station 50 to the punch station 60, and during the indexing movements at the punch station, the sealing membrane transport mechanism is actuated in conjunction with the rack support transport mechanism to ensure that the web of sealing membrane 90 is moved together with the rack support 30. This arrangement ensures a synchronised movement of the array of tubes with the sealing web, such that that the tension in the sealing web will not get too high.

The punch tool 62 is preferably mounted to the apparatus 10 with horizontal float so as to accommodate some initial misalignment of the punch tool, specifically the cutting edge(s) 66 thereof, with the rims 43 of the tubes 42 in the array.

Instead of the sealing station 50 and the punch station 60 being at fixed locations in the apparatus, and the rack support carriage 30 translating the array of tubes 42 therebetween, the rack support 30 may be fixed in the interior of the apparatus with the sealing and punch stations 50, 60 being translated horizontally into positions overlying the tubes for the respective sealing and punching operations.

Likewise, rather than the sealing platen 52 and punch tool 62 being lowered towards the rack support 30 to perform their respective operations, the rack support 30 may instead be raised towards the sealing platen 52 punch tool 62. It is the relative motion of the platen or punch tool and the support 30, and hence the rims 43 of the tubes 42 in the array that is important.

Whereas the web 90 is described as being supplied on a continuous roll 92, it may instead be supplied in single sheets, each transported individually to the sealing station 50 either by an adapted web transport mechanism or manually.

Rather than being operated in an automated manner within a sealing/punching apparatus, the described punch tool 60 could be used independently for separating individual tubes 42 from a pre-sealed array. Such independent use could be manual or could be automated in a simple punch apparatus.

In the foregoing description, the processing of fully populated racks of tubes has been described. It will be appreciated that that is not necessary and that instead only partially populated racks—i.e. racks having gaps where tubes could have been received—could be processed using the same apparatus and techniques.

An adaptation of the punch tool 62 is described with reference to FIGS. 10a-d. In this embodiment, the gripper punch tool 162 corresponds substantially to the punch tool described in the preceding Figures and referenced by numeral 62, but the ejector pins 168 can be selectively actuated between raised and lowered positions. Operation of the gripper punch tool 162 substantially corresponds to that of the punch tool 62, with the tool being lowered so that the cutting edges 166 pierce through the web of sealing membrane 190 to separate each tube 142 from the remainder of the web 190. The main difference is that the friction between the separated tubes 142 and the cutting edges 166 can be used to advantage, to lift selected ones of the separated tubes from the array.

Figure 10A:
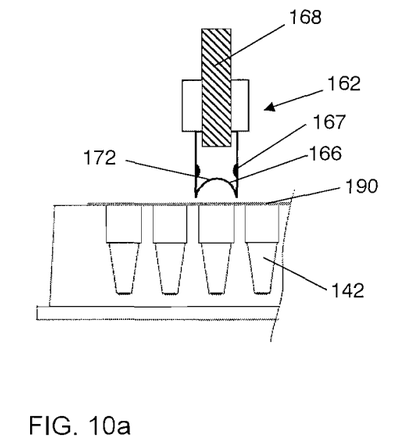
FIG. 10a is a schematic cross-section of an alternative application of the punch tool, corresponding in principle to FIG. 8a, but with the ejector pin raised.
Figure 10B:
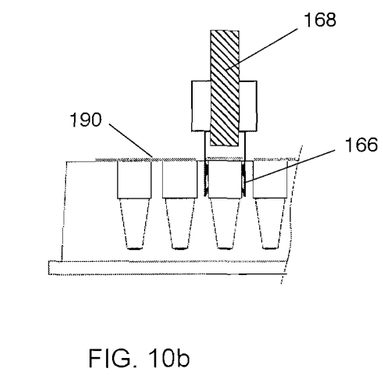
FIG. 10b corresponds to FIG. 10a, but showing the punch tool in a lowered position, piercing the membrane around the selected tube(s)
Figure 10C:
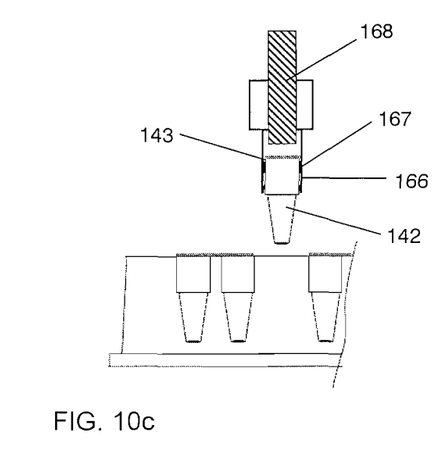
FIG. 10c corresponds to FIGS. 10a and 10b, but showing the punch tool in a raised position once again, a tube held in the cutting edge by friction.
Figure 10D:
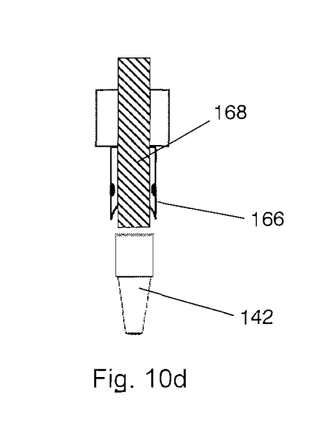
FIG. 10d shows the ejector pin in an eject position to push the tube out of the punch tool.

As shown in FIG. 10a-c, with the ejector pins 168 actuated to the raised position, the lowering and raising again of the punch tool 162 so that the cutting edges 166 cut through the web 190 results in the lifting of the separated sealed tubes 142 from the array. The gripper punch tool 162 can then be translated to a destination location, at which point a selected ejector pin 168 can be actuated to its lowered position to eject the associated tube 142 from the tool (FIG. 10d).

Inwardly-protruding nib features 167 may be provided within the cutting edge 166 to ensure a firm, interference grip with the tube 142. The nibs 167 may be located at the top of the cutting edge 166, for example at the interface with the tool body, to engage the rim 143 of the tube 142 only when the tube is fully received in the cutting edge 166. The nib features 167 may provide a positive indication of gripping engagement, for example by a 'click'.

As with the punch tool 62, the gripper punch tool 162 may comprise a single cutting edge corresponding to a single tube 142, or may comprise multiple cutting edges, in a linear or a 2D array. Where it comprises multiple cutting edges, it has a corresponding multiple of ejector pins, each of which can be actuated independently of the others. It is envisaged that the gripper punch tool 162 could be used on pre-punched tubes (i.e. on an array of tubes as sealed and separated by the apparatus described above). In this embodiment, the 'cutting' edges 166 would have to be thin, to fit between adjacent tubes 142, but would not necessarily need to have sharp lower edges on the 'blades' 172; they could therefore be called 'separating' edges 166.

As with the punch tool 62, the gripper tool 162 is able to be operated purely from above the arrays of tubes, there being no need for anything other than a support beneath the storage rack. As with the cutting edge(s) of the punch tool 62, the separating edge(s) 166 are preferably profiled so as to assist in aligning the tool to the array of tubes 142.

Typically, the storage rack will be held stationary, with the gripper tool 162 being translated into position to perform the gripping and lifting operation and then being translated to a dispense location—such as another storage rack. However, the relative motion may be reversed, with the gripper tool 162 being stationary and the storage rack(s) being moved into position for the gripping and lifting and dispense operations.

The invention claimed is:

1. A punch tool for separating individual tubes from an array of tubes within a storage rack, wherein upper rims of the tubes are sealed with a sealing membrane extending across the array, the punch tool having:
   a tool body;
   a cutting edge on a lower side of the tool body, configured to insert between adjacent tube rims so as to pierce through the sealing membrane around one of the sealed tube rims to separate the associated sealed tube from the remainder of the sealing membrane whilst the tubes remain within the storage rack; and
   an ejector pin insertable inside the cutting edge so as to be urged against the tube rim of the separated sealed tube.

2. The punch tool of claim 1, wherein the ejector pin is resiliently mounted to the tool body inside the cutting edge so as to be urged against the tube rim of the separated sealed tube with a predefined force.

3. The punch tool of claim 1, comprising a plurality of cutting edges configured to pierce through the sealing membrane around a corresponding plurality of the sealed tube rims so as to separate the respective sealed tubes individually and simultaneously from the remainder of the sealing membrane.

4. The punch tool of claim 3, wherein the plurality of cutting edges comprises a linear array for separating a corresponding linear array of tubes.

5. The punch tool of claim 3, wherein the plurality of cutting edges comprises a 2D array for separating a corresponding 2D array of tubes.

6. The punch tool of claim 1, wherein the cutting edge is profiled so as to cut through the sealing material in a progressive shearing action.

7. The punch tool of claim 6, wherein the cutting edge is substantially rectangular, comprising a piercing tip at each corner, and an inverted U- or V-shaped blade extending between adjacent piercing tips.

8. The punch tool of claim 1, further comprising a compression plate surrounding the cutting edge and having a flat lower surface resiliently mounted to the tool body so as to be urged against the web of sealing membrane with a predefined force.

9. Apparatus for separating individual sealed tubes from an array of tubes sealed with a membrane, the apparatus comprising:
   a rack support for supporting an array of tubes within a storage rack within the apparatus, wherein upper rims of the tubes are disposed in a plane; and
   a punch station comprising a punch tool having a tool body, a cutting edge on a lower side of the tool body and configured to insert between adjacent tube rims so as to pierce through the sealing membrane around one of the sealed tube rims to separate the associated sealed tube from the remainder of the sealing membrane whilst the tubes remain within the storage rack, and an ejector pin insertable inside the cutting edge so as to be urged against the tube rim of the separated sealed tube;
   wherein the cutting edge is moveable relative to the rack support to a position overlying the rack support and perpendicular to the plane between a position above the plane and a position below the plane.

10. The apparatus of claim 9, further comprising a sealing station having a platen with a lower platen surface moveable relative to the rack support to a position overlying the rack support and perpendicular to the plane between a position above the plane and a position substantially aligned with the plane, wherein the platen when in the position overlying the rack support and substantially aligned with the plane is configured to apply heat and/or pressure to the sealing membrane for sealing the membrane to the rims of a plurality of the tubes.

11. The apparatus of claim 10, further comprising a sealing membrane transport mechanism for supplying a web of sealing membrane to the sealing station, whereby at least a portion of the web of sealing membrane is disposed between the lower platen surface and the plane.

12. The apparatus of claim 10, wherein the punch station and the sealing station are each at respective fixed locations, the apparatus further comprising a rack support transport assembly for transporting a storage rack within the rack support in the apparatus, to the sealing station and then to the punch station.

13. The apparatus of claim 9, wherein the array of tubes comprises a regular array of x columns by y rows of tubes.

14. The apparatus of claim 13, further comprising a plurality of cutting edges configured to pierce through the sealing membrane around a corresponding plurality of the sealed tube rims so as to separate the respective sealed tubes individually and simultaneously from the remainder of the sealing membrane;
wherein the plurality of cutting edges comprises a linear array for separating a corresponding linear array of tubes; and
wherein the cutting edge is configured to pierce around each of the sealed tube rims of a column of the array simultaneously.

15. The apparatus of claim 14, wherein the punch station and the sealing station are each at respective fixed locations, the apparatus further comprising a rack support transport assembly for transporting a storage rack within the rack support in the apparatus, to the sealing station and then to the punch station;
wherein the rack support transport assembly is further configured to index the rack support at the punch station by the pitch of a column so as to align the cutting edge with the next column in the array.

16. The apparatus of claim 11, wherein the web of sealing membrane is continuous and the sealing membrane transport mechanism is configured to move the continuous web together with the storage rack during the transport of the storage rack from the sealing station to the punching station and, where the rack transport assembly is further configured to index the storage rack at the punch station, during that indexing.

17. The apparatus of claim 9, wherein the punch tool is mounted to the apparatus with lateral float.

18. A gripper tool for selectively lifting individual tubes from an array of tubes within a storage rack, comprising:
a gripper tool body;
a separating edge on a lower side of the tool body, configured to insert between adjacent tubes in the array and to grip an outer surface of a selected tube with an interference fit; and
an ejector pin mounted to the gripper tool body inside the separating edge and actuatable from a raised position, in which the selected tube can be received within the separating edge, and a lowered position, in which the selected tube is prevented from being received in the separating edge or, if already received therein, is ejected therefrom.

19. The gripper tool of claim 18, wherein the tool is additionally for separating individual tubes from an array of tubes within a storage rack, wherein upper rims of the tubes are sealed with a sealing membrane extending across the array, wherein the separating edge comprises a cutting edge, configured to pierce through the sealing membrane around the selected sealed tube rim so as to separate the associated sealed tube from the remainder of the sealing membrane prior to gripping the outer surface of the tube with an interference fit.

20. The gripper tool of claim 18, comprising a plurality of separating edges configured to grip a corresponding plurality of selected tubes so as to grip the respective selected tubes individually and simultaneously.

\* \* \* \* \*